United States Patent [19]

Shively et al.

[11] Patent Number: 5,081,235
[45] Date of Patent: Jan. 14, 1992

[54] CHIMERIC ANTI-CEA ANTIBODY

[75] Inventors: John E. Shively, Arcadia; Arthur D. Riggs, La Verne, both of Calif.; Michael Neumaier, Bonn, Fed. Rep. of Germany

[73] Assignee: City of Hope, Duarte, Calif.

[21] Appl. No.: 385,102

[22] Filed: Jul. 26, 1989

[51] Int. Cl.5 .............................................. C07H 17/00
[52] U.S. Cl. ....................................................... 536/27
[58] Field of Search .......................................... 536/27

[56] References Cited

PUBLICATIONS

Sahagan et al., J. Imm., 137(3):1066–1074, 1986.
Chen et al., Mol. Cell. Biol., 7(8):2745–2752, 1987.
Bergman et al., Proc. Nat. Acad. Sci., 81:7041–7045, 1984.
A. Liu et al., PNAS, 84:3439–3443, 1987.
L. Sun et al., PNAS, 84:214–218, 1987.
C. Beidler et al., J. Imm., 141(11):4053–4060, 1988.

Primary Examiner—John W. Rollins
Attorney, Agent, or Firm—Edward S. Irons

[57] ABSTRACT

A chimeric anti CEA antibody comparable to ATCC Accession No. BH 8747 is described.

2 Claims, 5 Drawing Sheets

```
gatcctggtc tacagtgtga ggtactggac aaccaagaat agagaaacct gtctcaaaaa aatgtattta    70
gaagggtccc ttaagacaca tgtgatgttc tagtaaattt tctgctaaca ccaacttcct ctgggtgaaa   140
caggggcagg tgcacatgga gaaacagtac atactcctgct gattgcata tgaaataatt tataacagcc   210
caggcttctt taaggcagct gccaggagcc taataaagca tccttcttc cagctcctcag ag atg gag   278
                                                                    M   E
aca gac aca ctc ctg cta tgg gtg ctc    gtga gggtgccgag                          335
 T   D   T   L   L   L   W   V   L <G
aagtgttgag agaaaccct ctgtggacat catgattttg cttgcctgtg ggttcataaa cataataatt    405
aacgcactttg taattggttt tgtttcctga gaccccttca tttcctggtt tctcatagga tgtccgcaat   475
atcctttgata tttttaaatg aaaaggtccc tgctgggaag gctttttacac ataaataaca gtagtctgtg  545
tgtttatcat tccag gt tcc aca ggt gac att gtg ctg acc caa tct cca gct tct ttg    604
                G > S   T   G   D   I   V   L   T   Q   S   P   A   S   L gct gtg tct ctt ggg cag agg gcc acc atg tcc tgc aga gcc ggt gaa agt gtt gat    661
 A   V   S   L   G   Q   R   A   T   M   S   C   R   A   G   E   S   V   D att ttt ggc gtt ggg ttt cac ttg tac cag cag aaa cca gga cag cca ccc aaa        718
 I   F   G   V   G   F   H   L   Y   Q   Q   K   P   G   Q   P   P   K ctc ctc atc tat cgt gca tcc aac tcc atc ctc att gat cct gtg gag gct gat gtt    775
 L   L   I   Y   R   A   S   N   L   E   S   G   I   P   V   E   A   D   V act ggg tct agg aca gac ttc acc ctc acc atc aat gag gat ccg tac acg ttc gga ggg acc   832
 T   G   S   R   T   D   F   T   L   T   I   N   E   D   P   Y   T   F   G   T gcc acc tat tac tgt cag caa act aat gag gat ccg tac acg ttc gga ggg acc        889
 A   T   Y   Y   C   Q   Q   T   N   E   D   P   Y   T   F   G   G   T aag ctg gaa ata aaa c gtaagtag tctttctcaac tcttgttcac taagtctaac cttgttaagt    946
 K   L   E   I   K <R gttcttttgtt gtgtgttttt cttaaggaga tttcaggat ttagcaaatt ccattctcag a            1007
```

FIG.1A

```
cgaccccaaa aaaccttgat tagggtgatg gttgcacgta gtggccattg gccctgatag acgttttttc   70
gcccctttgac gttggagtcc acgttcttta atagtggact cttgttccaa cttctccagc tggaatgtcc  140
ttatgtaaga aagcttgcc tcatggtat gcaaatcatg tgcgactgtg atgatcaata tagggatatc    210
cacaccaaac accatatgag ccctatcttc tctacagaca ctgaatctca aggtccttac a atg        274
                                                                     M
aaa tgc agc tgg gtt atc ttc ttc ctg atg gca gtg gtt aca g gtaag ggctcccaag    332
 K   C   S   W   V   I   F   F   L   M   A   V   V   T  <G tcccaaactt gagggtccat aaactctgtg acagtggcaa tcactttgcc tttcttttcta cag gg> gtc 400
                                                                           V
aat tca gag gtt cag ctg cag cag tct ggg gca gag ctt gtg gag cca ggg gcc tca   457
 N   S   E   V   Q   L   Q   Q   S   G   A   E   L   V   E   P   G   A   S gtc aag ttg tcc tgc aca gct tct ggc ttc aac att aaa gac acc tat atg cac tgg   514
 V   K   L   S   C   T   A   S   G   F   N   I   K   D   T   Y   M   H   W gtg aag cag agg cct gaa cag ggc ctg gaa tgg att gga agg att gat cct gcg aat   571
 V   K   Q   R   P   E   Q   G   L   E   W   I   G   R   I   D   P   A   N ggt aat agt aaa tat gtc ccg aag ttc cag ggc aag gcc act ata aca gca gac aca   628
 G   N   S   K   Y   V   P   K   F   Q   G   K   A   T   I   T   A   D   T tcc tcc aac aca gcc tac ctg cag ctc agc ctg aca tct gag gac act gcc gtc       685
 S   S   N   T   A   Y   L   Q   L   S   L   T   S   E   D   T   A   V tat tat tgt gct ccg ttt ggt tac tac gtg tct gac tat gct atg gcc tac tgg ggt   742
 Y   Y   C   A   P   F   G   Y   Y   V   S   D   Y   A   M   A   Y   W   G caa gga acc tca gtc acc gtc tcc tca g gta agaatggcct ctccaggtct ttattttaa    799
 Q   G   T   S   V   T   V   S   S cctttgtatg gacttttctg aacattgcag actaatcttg gatatttgtc ctgaggga..........    856
```

| | A | | | B | | |
|---|---|---|---|---|---|---|
| | 1 | 2 | 3 | 1 | 2 | 3 |

| | A | | | B | | |
|---|---|---|---|---|---|---|
| | 1 | 2 | 3 | 1 | 2 | |

—200K
—97K
—68K
—43K
—29K
—18K

CHIMERIC ANTI-CEA ANTIBODY

Carcinoembryonic antigen (CEA) is extensively used in the in vitro immunodiagnosis of human colon adenocarcinomas. This invention relates to a chimeric anti-CEA antibody.

BACKGROUND OF THE INVENTION

CEA is the best characterized human tumor-associated antigen and the most widely used tumor marker for the in vitro diagnosis of human colon cancers. CEA, however, is one of a family of closely related genes including normal cross-reacting antigen (NCA) and biliary glycoprotein (BGPI).

Many antibodies to tumor markers cross-react with related antigens. Accordingly, the development of antigen-specific monoclonal antibodies (MABs) for in vitro and in vivo diagnosis and therapy requires a good knowledge of the number, quality and biodistribution of related cross-reactive antigens. This requirement has restricted the number of acceptable tumor markers which, in the case of colon cancer, includes CEA, CA 17-1A and TAG-72.

Careful immunochemical characterization of the MAB to be used is required with respect to its specificity and affinity for the target antigen and for related antigens. Systematic application of a MAB that is cross-reactive with a related antigen must be avoided to foreclose risk of potentially severe side effects.

Murine MAB T84.66 (ATCC Accession No. BH 8747) IgGI,k shows high affinity constant ($2.6 \times 10^{10} M^{-1}$) and no cross reactivity to other members of the CEA gene family. T84.66 is therefore ideally suited for immunodetection and immunotherapy studies.

Use of murine MABs including T84.66 for detection and therapy of human tumors is constrained by patient immune response against the heterologous immunoglobulin. The production of human anti-mouse antibodies (HAMA) leads to reduced efficiency of the MAB and to potentially serious manifestations of acute and chronic allergic complications for the patient. See Levy, et al. *Ann. Rev. Med.* 34:107–116 (1983); Houghton, et al. *Proc. Natl. Acad. Sci. U.S.A.*, 82:1242–1246 (1985) and Sears, et al. *J. Biol. Resp. Modifiers* 3:138–150 (1984).

Recombinant DNA technology provides attractive methods to generate MABs useful to circumvent such problems from chimeric human/non-human genes. In addition, recombinant antibody genes provide a renewable source of antibodies which can be further engineered to alter affinity constants and effector functions. Using different approaches, a number of antibody genes and derivatives thereof have been constructed which code for antibody chimeras directed against tumor-associated antigens. Sahagen, et al, *J.Immunol.* 137:1066–1074 (1986); Sun, et al., *Proc.Natl.Acad.Sci.U.S.A.* 84:214–218 (1987); Nishimura, et al., *Cancer Res.* 47:999–1005 (1987); Liu, et al. *Proc.Natl.Acad. Sci.USA* 84:3439–3443 (1987).

Beidler, et al, *J. Immunology* 141:4053–4060 (1988) describe a murine/human chimeric antibody constructed by using variable light and variable heavy regions from a murine hybridoma CEM231.6.7 specific for CEA. The parental hybridoma bound antigen with an affinity of $5 \times 10-9M^{-1}$, chimeric subclones bound antigen at $2 \times 10^{10}M^{-1}$, and $1 \times 10^{10}M^{-1}$. Clinical utility of the chimera, including lack of cross-reactivity was not demonstrated.

SUMMARY OF THE INVENTION

This invention includes the cloning and sequencing of the genes coding for MAB T84.66, the amino acid sequence of the variable regions for the light and heavy chains, and the construction of mouse/human chimeric IgG-1 antibody genes using T84.66 variable region genes and human constant region genes. The gene constructs were transfected into murine myeloma cells (Sp2/0) by electrophoration and into CHO cells by lipofection. The chimeric antibodies exhibited a specificity and affinity for CEA similar to that of the T84.66 immunoglobulin produced by the murine hybridoma cell line.

MATERIALS AND METHODS

Construction of Genomic Libraries

Hybridoma DNA was extracted according to standard procedures, (see Maniatis T., et al., in Molecular cloning: a laboratory manual, Cold Spring Harbor, New York (1982) and Meese, E., et al., *Gene Anal. Techn.* 4:45–49 (1987)) partially digested with Mbo I or completely restricted with Eco R I. Partially digested DNA was fractionated on a sucrose gradient (see Meese, *Gene Anal. Techn.*, supra) and fragments of 15–20 kb were cloned into A-FIX (Stratagene, San Diego, Cal.) according to the manufacturer's recommendations. Eco R I restricted DNA was run on a preparative 0.7% LMT agarose gel (BRL). Appropriate DNA fragments were purified from the gel by extractions with hot phenol/$CHCl_3$ and were subsequently ligated into the Eco R I site of Lambda-ZAP (Stratagene). In vitro packaging reactions were performed using Gigapack packaging extracts (Stratagene).

Probes, Primers and Sequencinq

Plaque screening (Benton, W. D., et al., *Science*, 196:180–182 (1977) for the T84.66 kappa light chain gene was done with an 800 pb Pst I cDNA fragment from pK94 representing the murine $C_k$ region gene.

Screening for the murine heavy chain gene was performed using a 991 base pair (bp) Xba I fragment from the mouse enhancer region. (See Gillies, et al., *Cell* 33:717-728 (1983)), a 1.5 kilobase (kb) cDNA fragment from the heavy chain constant region gene of hybridoma CEA.66-E3 (Cabilly, et al., *Proc.Natl.Acad.-Sci.USA* 81:3273-3277 (1984) and a 5.4 kb EcoRI fragment containing an aberrantly rearranged heavy chain from Sp2/0.

Positive clones were further characterized by hybridization to a panel of J-region oligonucleotides as shown in Table I.

TABLE I

Oligonucleotides Used As Probes and Sequencing Primers

| Sequence of Oligonucleotide | | Type of Rearrangement | | | | | |
|---|---|---|---|---|---|---|---|
| | | Germline | J1 | J2 | J3 | J4 | J5 |
| *Kappa light chain gene* | | | | | | | |
| Jκrearr | 5'AGCTTTCGCAGCTACCC | + | | | | | |
| Jκ1 | 5'GTTTGCATTCATCTTAGGT | + | + | | | | |
| Jκ2 | 5'AGAAGAGTTGAGAACAAGT | + | + | + | | | |
| Jκ3 | 5'GGATTCATGTAAAAACGAG | + | + | + | + | | |
| Jκ4 | 5'TCAACCTTTATTTTGCATTC | + | + | + | + | + | |
| Jκ5 | 5'CTTTGCATTCATGTGAA | + | + | + | + | + | + |
| κ138 | 5'CGTGTAAGCTCCCTAAATG[1] | | | | | | |
| *Gamma Heavy chain gene* | | | | | | | |
| Jγrearr | 5'CACAGTCTCTGTTCTGCC | + | | | | | |
| Jγ1 | 5'GGTGACCGTGGTCCCTGC | + | + | | | | |
| Jγ2 | 5'TGTGAGAGTGGTGCCTTG | + | + | + | | | |
| Jγ3 | 5'CTGCAGAGACAGTGACCA | + | + | + | + | | |
| Jγ4 | 5'GCCATTCTTACCTGAGGA | + | + | + | + | + | |

[1]specific for aberrantly rearranged kappa light chain gene in Sp2/0 hybridoma fusion partner cells. See Cabilly, et al., Gene. 40: 157-161 (1985)

Oligonucleotides Jδ1 through Jκ5 were used to identify specific VJ rearrangements in murine kappa light chain genes and Jκrearr was used to distinguish between active and germline configuration genes (GENbank entry J0228). Oligonucleotide κ138 was used to screen for the aberrantly rearranged kappa gene κ138 (Cabilly, et al. *Gene,* 40:157-161 (1985) in the T84.66 fusion partner cell line Sp2/0. Oligonucleotides Jγ1 through Jγ4 were used to identify VDJ rearrangements of the murine heavy chain genes, and probe Jγ7 rearr was used to distinguish the active from the germline configuration (GENbank entry J00440). In addition, oligonucleotide probes were designed for the N-terminal region of both T84.66 genes according to DNA sequencing data to allow upstream characterization of the promoter regions. These sequences for kappa and gamma chain genes were 5'TGGGTCAG-CACAATGTC and 5'CTGCTGCAGCTGAACCTC, respectively.

Probe $^{32}$P-labelling and Southern blot and dot blot hybridizations were done as described in Maniatis T., et al., in Molecular cloning: a laboratory manual, Cold Spring Harbor, N.Y. (1982) and Feinberg, A. P., et al., *Anal. Biochem.* 132:6-13 (1983). DNA sequence analysis of both strands of the variable region genes was performed on both strands by the dideoxynucleotide chain termination method of Sanger.

Figure 1A:
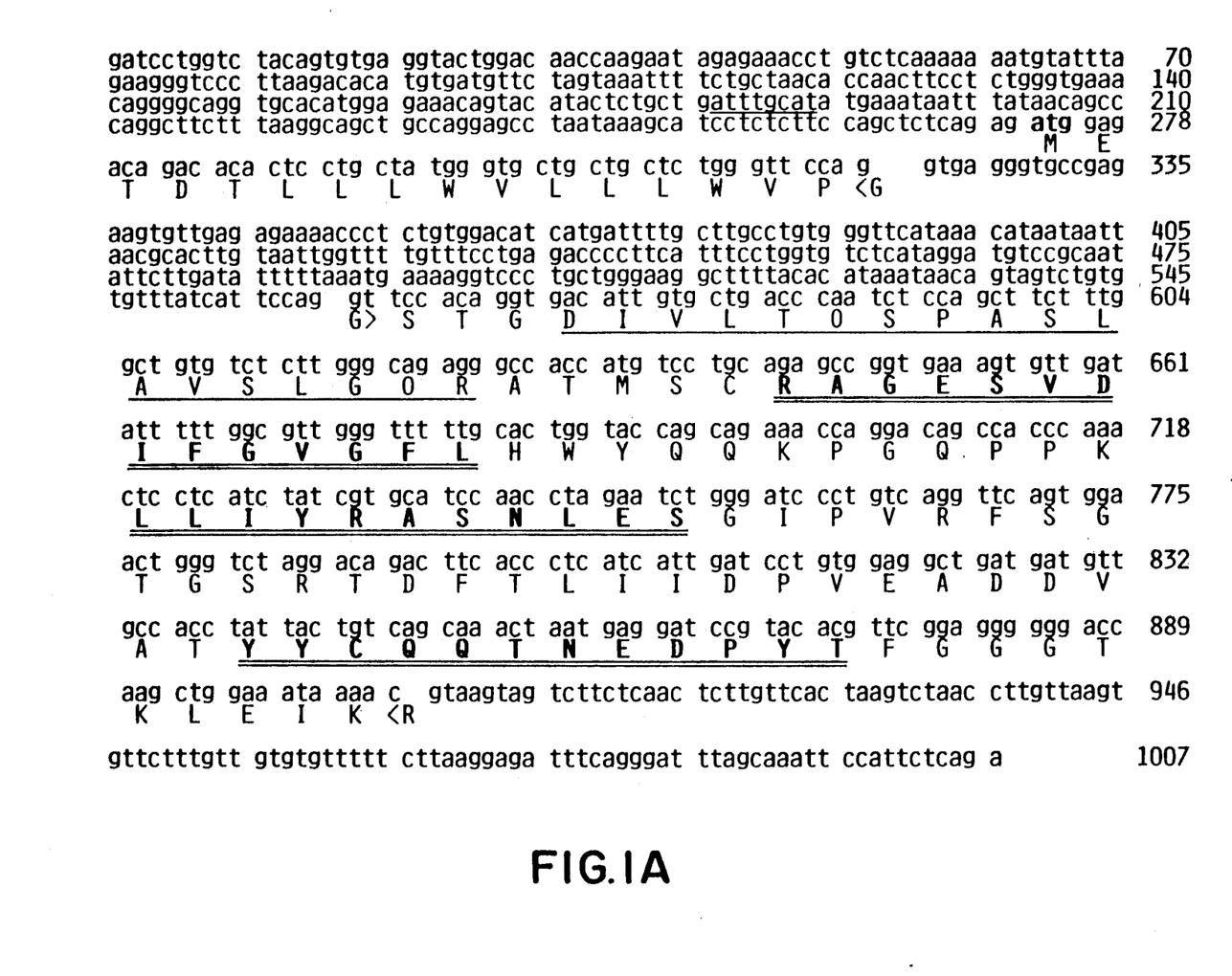
FIG. 1A is the sequence of the kappa light chain of the T84.66 monoclonal antibodies.
Figure 1B:
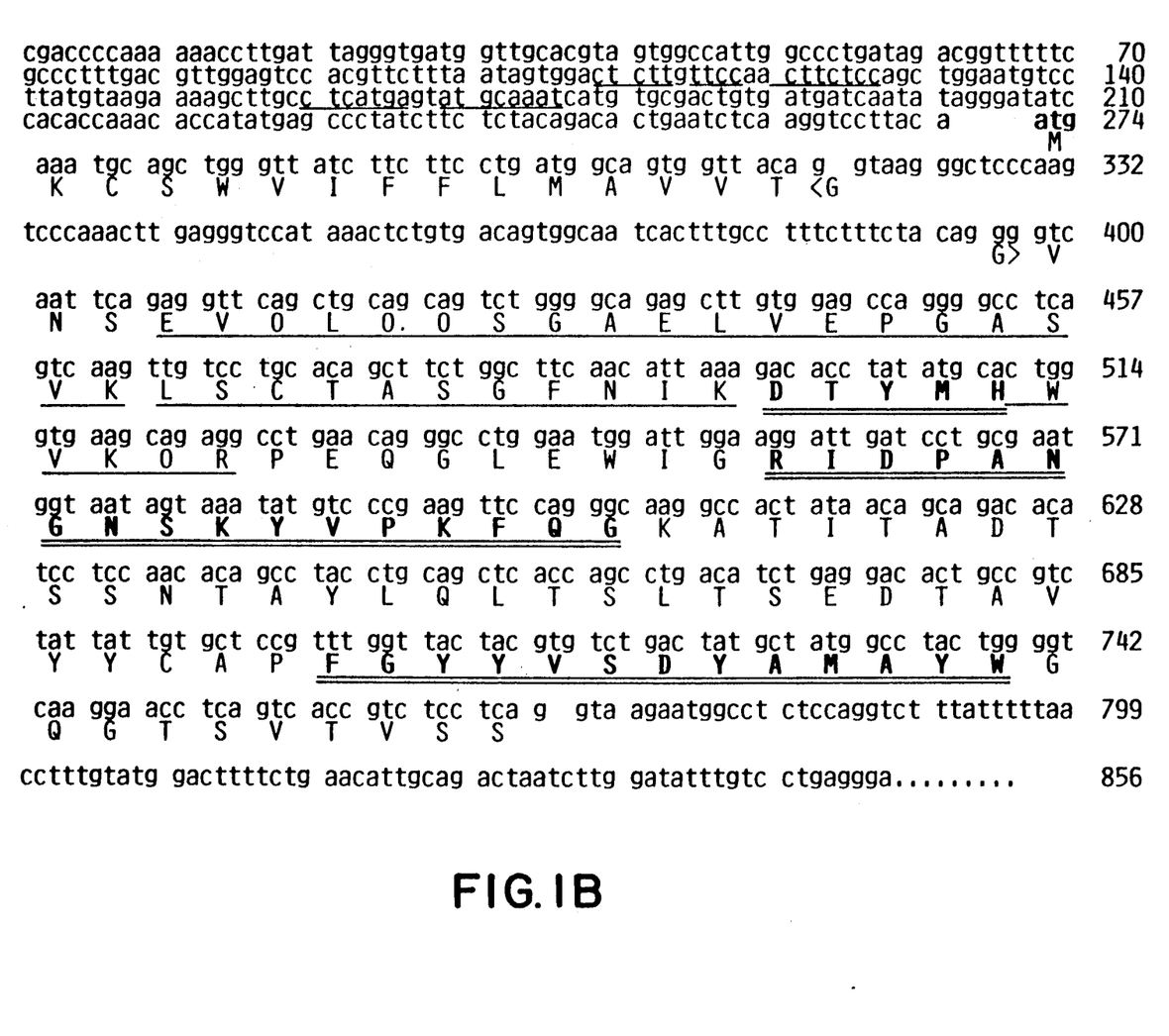
FIG. 1B is the sequence of the gamma heavy chain of the T84.66 monoclonal antibodies.

FIGS. 1A and 1B set forth the sequences of the light and heavy chain genes.

Nucleotides underlined in FIGS. 1A and 1B indicate the putative promoter regions. See Bergman, et al. *Proc.Natl.Acad. Sci.USA* 81:7041-7045 (1984) and Eaton, et al., *Proc.Natl.Acad. Sci.USA* 84:7634-7638 (1987). The start codons are shown in bold. Underlined amino acids indicate where protein sequence data was obtained by analysis of tryptic peptides. The double underlined regions are the complementarity determining regions.

Construction of The Chimeric Kappa Gene

Positive clones from the Lambda-FIX library were subcloned into Bluescribe and Bluescript plasmids (Stratagene). For construction of the chimeric kappa gene, the Bluescript vector was modified by site-directed mutagenesis using the MutaGene System (BioRad). Specifically, the unique Xmn I site located in the ampicillin resistance gene was eliminated from the vector by a silent mutation. The sequence of the mutagenic oligonucleotide was 5'GAAGAGCGTTTTCCAATG. The substituted base is shown in bold and underlined. After assembly in Bluescript (FIG. 2A) the completed chimeric gene was transferred into the expression vector pcDneo (See Chen, C., et al., *Mol.Cell.Biol.* 7:2745-2752 (1987)). DNA used for transfection was purified as described in Toneguzzo, et al, *Proc.Natl-.Acad.Sci.USA* 83:3496-3499 (1986) and used for transfection either as supercoiled DNA or after restriction with Cla I.

Construction of The Chimeric Gamma Gene

Positive clones from the Lambda-ZAP library were subcloned and further characterized by DNA-sequencing using as primers Jγ4- and the N-terminal heavy chain oligonucleotides. The chimeric T84.66 heavy chain gene was assembled in Bluescript and recloned as a Xho I/Not I fragment into the Sal I site of pcDneo by blunt-end ligation. Transfection was done with either supercoiled or Cla I restricted DNA.

Transfection and Culture of Sp2/0 and CHO Cells

The chimeric light and heavy chain expression plasmids were cotransfected into Sp2/0 cells by electroporation (see Potter, H., *Anal. Biochem* 174:361-373 (1988)), and into CHO cells by lipofection (Felgner, et al., *Proc.Natl.Acad.Sci.USA* . 84:7413-7417 (1987)). Twenty μg of each linearized plasmid was added to 1.5×10$^6$ Sp2/0 cells in 0.7 mM sodium phosphate/20 mM HEPES/6 mM glucose in a volume of 0.8 ml. The cells were incubated at 4° C. for 10 min., and electroporated with one 100 μsec pulse at 200 V and 900 μF. The electroporated cells were incubated in 5%

$CO_2$ at 37° C. for 48 hours in Opti-MEM media (Gibco) with 10% FCS, then grown under selection conditions with 800 μg/ml of (G418) (Gibco) for two weeks. Twenty μg of supercoiled plasmids were cotransfected into CHO cells using Lipofectin and the manufacturer's protocol (BRL). The cells were incubated at 37° C. and 5% $CO_2$ for 24 hours in Ham's F12 media, after which media containing 10% FCS was added. After an additional 48 hours, the cells were transferred to selective media (Ham's F12) containing 800 g/ml of G418. After two weeks of selection, the cell supernatants were screened for antibody production by EIA.

Transfectoma clones were cultured at 37° C. in 5% $CO_2$ in Opti-MEM containing 10% FCS. Several clones were adapted to serum-free medium (Excell-300, J. R. Scientific). CHO cells were cultured in 5% $CO_2$ at 37° C. in Ham's F12 medium (Gibco) containing 10% FCS. Ascites tumors were raised in Nude mice by injecting IP $5 \times 10^6$ cells in Opti-MEM; Ascitic fluid was harvested after 3–4 weeks, and the antibody purified on a protein A-Sepharose column (BioRad).

EIA For Chimeric Antibody Expression

Microtiter wells (Costar 2596) were coated with 0.1 mL of 2 μg/mL of CEA in carbonate buffer for 4 hours at 37° C., washed with 0.075M phosphate buffered saline (PBS), blocked with 1% bovine serum albumin (BSA) in PBS overnight at room temperature, and washed with PBS. Fifty μl of cell supernatant were added to each well, incubated for 90 min. at 37° C., washed, and incubated with 100 μl of goat anti-human γ-chain-alkaline phosphatase conjugate (TAGO #4600), goat anti-human κ-chain conjugate (TAGO #2496), or anti-human γ,κ-chains conjugate (TAGO #4600). The plates were incubated for 90 min. at 37° C., washed with ethanolamine buffer, incubated with 100 μl of p-nitrophenolphosphate substrate (Sigma) for 30 min. at 37° C. The reaction was stopped with 20 μl of 3N NaOH, at absorbance read at 410 nm.

Quantitation of Chimeric MAB

Microtiter plates were coated with goat anti-human Fc (Cappel 0601-0101) at 10 μg/ml in HPBS for 4 hours at 37° C., blocked with 10% BSA in PBS overnight at room temperature. Fifty μl of cell supernatants were added to each well, incubated for 90 min. at 37° C., washed, and incubated with 100 μl of goat anti-human Fc (Cappel 8601-0121). The remainder of the assay is the same as described above. The goat anti-human Fc conjugate was preabsorbed by passage over a mouse IgG affinity column (Cappel 7011-080). Human IgG was used in the range of 2–1000 ng/ml for a standard curve.

Anti-CEA activity was quantitated from a modified double MAB EIA (Roche) which uses T84.66E3 antibody enzyme conjugate. CEA standards were preincubated with increasing amounts of T84.66E3 antibody before addition of T84.66 antibody enzyme conjugate. The resulting inhibition curve (FIG. 5) was used to quantitate the amount of anti-CEA activity in the chimeric expression systems.

Protein Characterization of Chimeric MAB

Culture supernatants from serum free media were concentrated 5–10 fold in a centricon-10 (Amicon). Concentrated supernatants or purified MAB from ascites wee analyzed by SDS gel electrophoresis (see Laemli, U. K., *Nature* 277:680–685 (1970)) on 4–20% gradient gels under reducing (10% mercaptoethanol) and nonreducing conditions. The samples were boiled in dissociation buffer for 5 min. prior to analysis. The gels wee stained with Coomassie Blue or transferred to nitrocellulose (Millipore HAHY 305 FQ) at 300 mA for 2.5 hours (see Towbin, et al., *Proc.Natl.Acad.Sci.USA* 76:4350-4354 (1979)). Detection of chimeric MAB was performed with goat anti-human IgG peroxidase conjugate (BioRad 172-1050) which was affinity purified on a mouse IgG column as described above.

Protein Sequence Analysis of T84.66 Gamma Heavy and Kappa Light Chains

T84.66 MAB (5 mg) was reduced with 30 mM DTT in 1 ml of 0.5M Tris-HCl (pH 8.0), 1 mM EDTA for 2 hours, and alkylated under nondenaturing conditions with 60μ moles of iodoacetic acid for 30 min. in the dark under nitrogen. The solution was dialyzed vs 1M acetic acid, and chain separation was performed on a Sephadex G-100 column ($1.5 \times 50$ cm). The isolated chains gave single bands at 25 and 50 kDa on SDS gel electrophoresis, and single amino-terminal sequences. The heavy and light chains were reduced and alkylated under denaturing conditions in 6M guanidinium HCl essentially as described above. The samples were dialyzed vs 0.2M ammonium bicarbonate (pH 7.8), and digested with trypsin (1/50 by weight) for 18 hours at 37° C. Tryptic peptides were separated by reverse phase HPLC on a Vydac C-18 columns using a trifluoroacetic acid-acetonitrile gradient system. The peptides were subjected to microsequence and fast-atom bombardment/mass spectrometry analyses.

EXPERIMENTAL RESULTS

The T84.66 Kappa Light Chain Gene

The complete T84.66 kappa gene was cloned from a partial Mbo I library. Five positive clones were obtained after the first screening approximately one million plaques with a murine constant region probe, and these were further characterized for VJ-rearrangement by Dot Blot hybridization patterns with the J-region oligonucleotides. Only one clone showed a Jκ2-rearrangement pattern (see Table I) and was further analyzed. Hybridization to the appropriate synthetic probes occurred to a 2.8 kb Sst I fragment and a 5.2 Bam H I fragment. The two fragments were subcloned into Bluescribe and into a Bluescript derivative (XmnI site removed from $Amp^R$ gene) to give clone Bbe 2.8 and clone Bpt 5.2 respectively. Clone Bbe 2.8 contained the complete T84.66 variable region gene, the DNA sequence of which is shown in FIG. 1A. By comparison to published data, the T84.66 kappa chain belongs to subgroup 3 (see Kabat, et al., Sequences of proteins in immunological interest, U.S. Department of Health and Human Services, NIH 4th edition (1987)). The deduced amino acid sequence of the variable region was compared to protein sequence data obtained from tryptic peptides of purified light chain of T84.66. There was 100% identity with sequenced variable region peptides, which included the complementarity determining regions (FIG. 1A).

The T84.66 Gamma Heavy Chain Gene

Screening of the partial Mbo I library with the 991 bp XbaI murine heavy chain enhancer region probe resulted in a number of positive clones, but none of these contained the T84.66 variable region. Instead, we found that the clones positive for this probe were either in a germline configuration or truncated at the 5'-end or represented an aberrantly rearranged heavy chain gene. DNA sequence analysis of the aberrantly rearranged gene, using a primers the heavy chain specific J-region oligonucleotides Jγ2 and Jγ3, showed that this gene was generated by the joining of the Dq52 and Jγ2 minigenes with a subsequent head-to-head joining to the Jγ3 gene. The existence of this same aberrant gene has been reported in a different hybridoma cell line (Liu, Z-q., et al., Nucl.Acids.Res. 15:4688 (1987)), indicating that this gene was contributed to the T84.66 hybridoma by the Sp2/0 fusion partner.

Knowing this aberrant gene facilitated the identification of restriction fragments containing the T84.66 variable region. Southern blots of Eco R I digested T84.66 DNA were probed with the enhancer fragment and also with the 5.4 kb Eco RI fragment containing the aberrantly rearranged Sp2/0 gene. Both probes hybridized to bands of sizes of approximately 6.6 kb and 3.3 kb which represent the heavy chain gene in its germline configuration (Kataoka, et al, Proc.Natl.Acad.Sci. U.S.A. 77:919-923 (1980)) and its rearranged form, respectively (data not shown). The 3.3 kb fragment was cloned into Lambda-ZAP. After subcloning, one of the positive clones was further characterized, first by dot blots using J-region oligonucleotide probes and then DNA sequencing. The nucleotide sequence of the T84.66 heavy chain variable region gene is shown in FIG. 1B. The T84.66 heavy chain gene was generated by a joining even to Jγ4, and by comparison to published sequences can be assigned to subgroup 2c. Kabat, supra. The deduced amino acid sequence was in complete agreement with direct protein sequence data.

Construction of Chimeric Genes and Expression Vectors

Figure 2A:
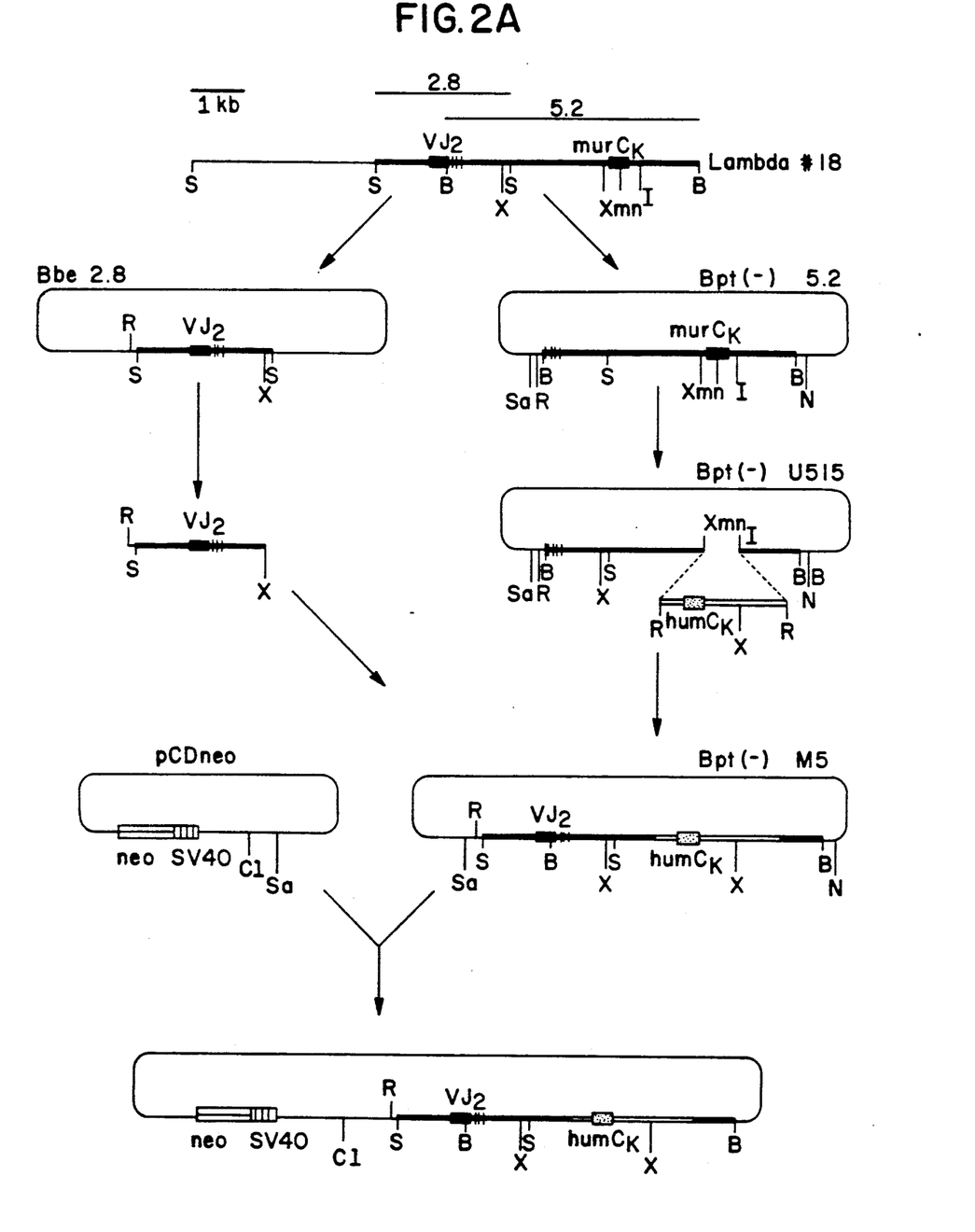
FIG. 2A shows the construction of a plasmid for the direct expression of the chimeric T84.66 kappa gene.

As illustrated in FIG. 2A, the murine kappa constant region gene exon was removed from the T84.66 kappa gene by Xmn I restriction of Bpt 5.2 and replaced with a blunt ended 2.5 kb Eco RI fragment containing the complete human kappa constant region (gift from Dr. Phil Leder) to yield clone Bpt 5.2 U515. The final chimeric T84.66 kappa gene was assembled by inserting a 2.6 kb Eco RI/ Xba I fragment from clone Bbe 2.8 into Bpt 5.2 U515, previously cut with Eco RI and partially with Xba I. The completed construct was then transferred as an Xho I/Not I fragment into the Sal I site of the expression plasmid pcDneo by blunt end ligation. The resulting clone was designated pcDneo M5.

Figure 2B:
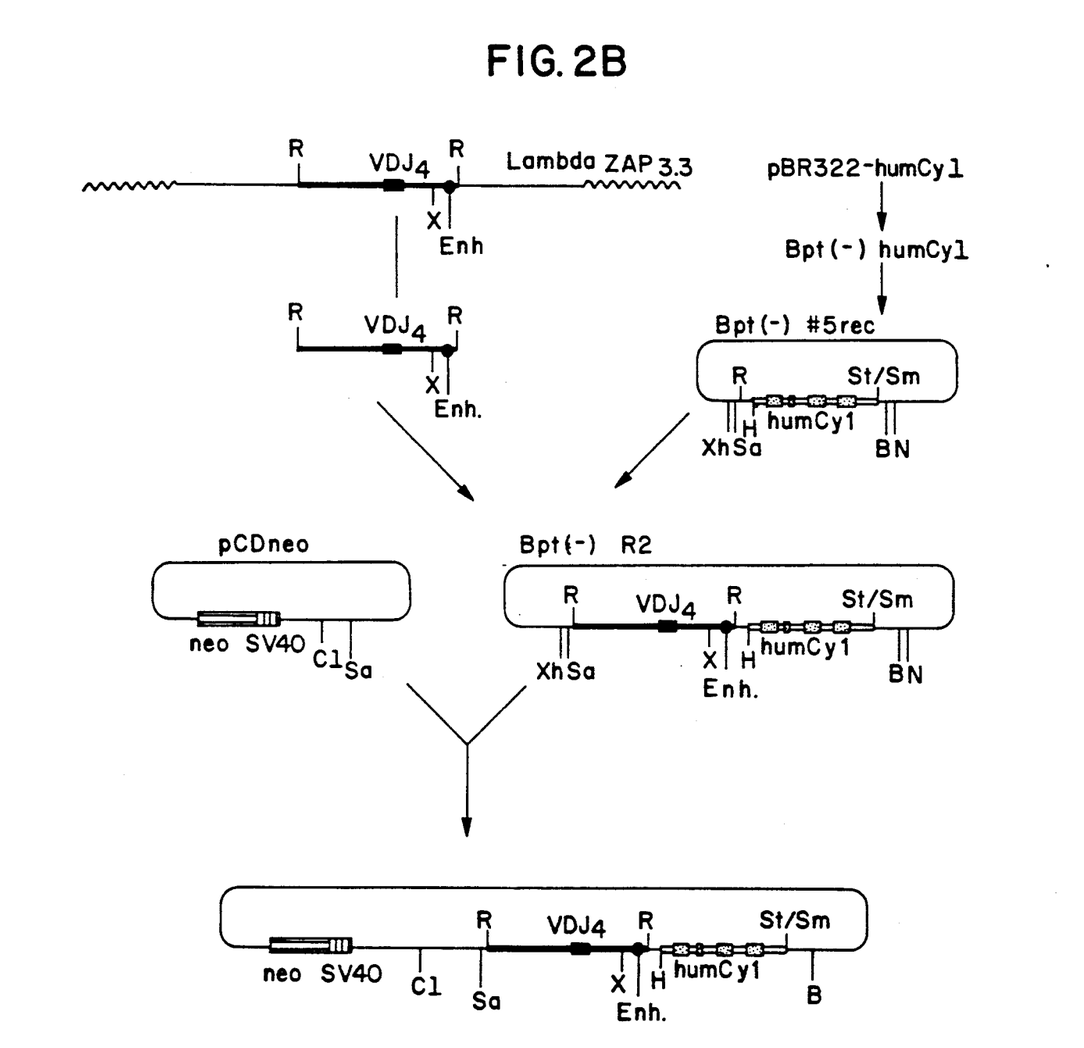
FIG. 2B shows the construction of a plasmid for the direct expression of the chimeric T84.66 gamma gene.

To create the human/mouse chimeric heavy chain construct (FIG. 2B), the human genomic IgGI constant region gene (gift from Dr. Phil Leder) was recloned as a Hind III fragment into the Bluescript polylinker in order to generate a 5' Eco RI site for further construction. A 2.2 kb Eco RI/ Stu I subfragment was then subcloned into the Eco RI/Sma I polylinker sites of Bluescript (Bpt#5rec). Finally, the 3.3 kb Eco R I fragment containing the T84.66 heavy chain variable region gene, its promoter, and the murine heavy chain transcription enhancer was ligated with clone #5rec which had been linearized at the Eco RI site. The chimeric T84.66 heavy chain gene from the resulting clone Bpt (−) R2 was recloned as an Xho I/Not I fragment into the Sal I site of pcDneo by blunt end ligation to form pcDneo R2.

Transfection of Chimeric Genes

The chimeric genes pcDneo M5 (kappa) and pcDneo R2 (gamma) were linearized at a unique ClaI site and cotransfected into Sp2/0 cells by electroporation, or into CHO cells by lipofection. After selection in G418 for two weeks, the supernatants of approximately 900 clones were screened for antibody production, and the higher producers were subcloned. For the Sp2/0 transfectants, several of the clones were grown as ascites in nude mice, and the antibody levels were quantitated (Table II). Initial experiments in which we attempted to grow ascites in Balb/c mice failed, presumably due to an immune response towards the cells producing chimeric antibody. This problem was later overcome by pristine pretreatment of the Balb/c mice.

Analysis of Chimeric MAB

Supernatants from transfected cells were adsorbed to CEA coated microtiter plate wells and the immune complexes were detected with anti-human kapa or gamma antibody-enzyme conjugates. Five clones producing relatively high levels were obtained from the transfection of Sp2/0, and six clones were obtained from cotransfection of the CHO cells. Subsequent to subcloning, one of the Sp2/0 clones lost the ability to produce Ig. The supernatants were quantitatively assayed for anti-human IgG and anti-CEA activity. The results are reflected in Table II.

TABLE II

| Quantitation of anti-CEA chimeric IgG | | | |
|---|---|---|---|
| | Secreted IgG[1] ng/ml | Secreted anti-CEA[2] ng/ml | Ascites IgG[3] µg/ml |
| Sp2/0 Transfectants | | | |
| 2 G | 160 | 340 | 720 |
| 11 H | 150 | 360 | 56 |
| 9 H | 240 | 360 | 320 |
| 1 F | 160 | 190 | 960 |
| CHO Transfectants | | | |
| 6 G | 15 | 50 | |
| 6 H | 40 | 70 | |
| 7 H | 60 | 70 | |
| 10 H | 40 | 80 | |
| 11 H | 30 | 60 | |
| 12 H | 70 | 70 | |

[1]Anti-human IgG activity was measured by EIA plates coated with goat anti-human Fc antibody, and captured antibody detected with goat anti-human γ-chain antibody/alkaline phosphatase conjugate. Samples were calibrated with purified human IgG, and values normalized to 10[7] cells/ml.
[2]Anti-CEA activity was determined by EIA in plates coated with CEA, and captured antibody detected as above. The assay was calibrated with purified clone 1F (mass determined by amino acid analysis). Similar values were determined in an EIA inhibition assay in which chimeric antibody was used to inhibit the binding of the parent hybridoma to CEA bound to another anti-CEA MAB on glass beads (Roche EIA). The assay was calibrated with the parent hybridoma T84.66.
[3]Assayed as described in footnote 1 above. The values are not corrected for cells/ml.

The clones (other than 12H) exhibited higher activities in the CEA assay than in the human IgG assay. The ratio of activities was comparable for all clones except 12H when purified chimeric antibody from clone 1F was passed over a CEA affinity column and the unbound antibody assayed for human IgG activity. None was observed. In a control experimented, 100% activity was recovered when human IgG was passed over the CEA affinity column.

Figure 3:
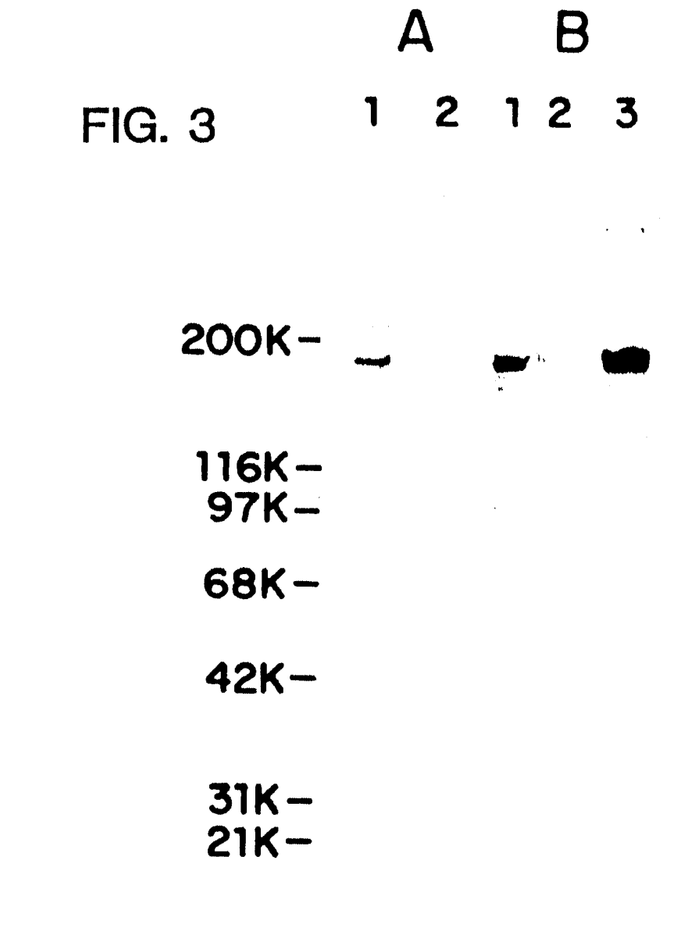
FIG. 3 is a Western Blot of non-reducing SDS PAGE of secreted chimeric anti-CEA antibody. Panel A: CHO cell supernatants: Lane 1, Human IgG standard; Lane 2, CHO supernatant. Panel B: Sp2/0 transfectoma supernatants: Lane 1, ascites from clone 1F; Lane 2, supernatant from clone 1F in tissue culture. The antibody used for detection was anti-human Fc antibody-enzyme conjugate. Panel B, Lane 3, Coomassie Blue staining of ascites from clone 1F.
Figure 4:
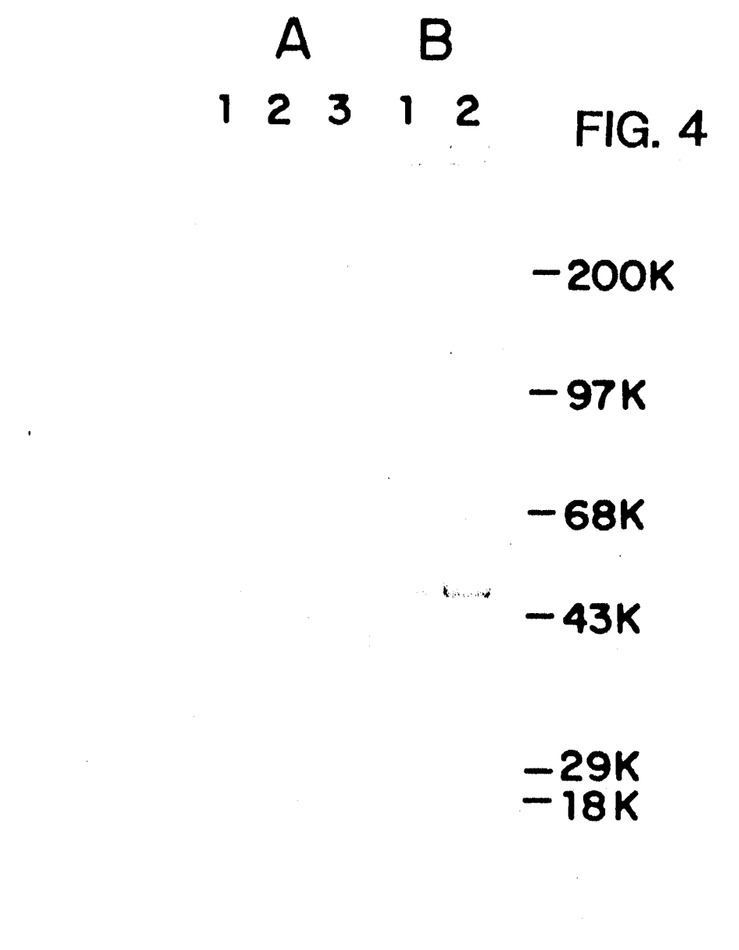
FIG. 4 is a Western Blot of reducing SDS PAGE of secreted chimerc anti-CEA antibody. Panel A: Lane 1, ascites from clone 1F; Lane 2, ascites from clone 9H; Lane 3, supernatant from clone 1F; Blots were stained using anti-human k,g polyclonal antibodies. Panel B: Coomassie Blue staining of gels: Lane 1, ascites from clone 1F; Lane 2, ascites from clone 9H.

From the 30 mice innoculated with antibody producing Sp2/0 transfectoma clones, the range of antibody production was from 56–960 µg/ml (Table II). For SDS PAGE and Western Blot analyses, the cells producing chimeric antibody were adapted to serum free media, the supernatants were concentrated, and IgG was purified by protein A-Sepharose affinity chromatography. Antibodies from transfectomas grown in ascites were purified and analyzed similarly. Chimeric antibodies from either Sp2/0 or CHO cells show major bands at 150 kD when transferred to nitrocellulose and stained with anti-human Fc antibody enzyme conjugate (FIG. 3). Coomassie Blue staining of purified IgG from ascites fluid also shows a major band at 150 kDa. Under reducing conditions, transfectoma-produced IgGs gave 50 kD and 25 kD heavy and light chain bands when visualized either by Coomassie blue staining or specific anti-human κ,γ-chain staining (FIG. 4). The chimeric antibody was also tested for CEA-specific binding on Western Blots. CEA and the normal cross-reacting antigen (NCA) were run on 7% SDS gels, transferred to nitrocellulose, incubated with chimeric anti-CEA, and detected with anti-human Fc antibody enzyme conjugate. The results (not shown) demonstrated that the chimeric antibody retained its specificity for CEA, and does not react with NCA.

Affinity Constant For Chimeric Anti-CEA

Purified antibody from the ascites fluid of transfectoma clone F1 was analyzed in a noncompetitive EIA to determine the affinity constant. Antibody from clone F1 had an affinity constant of $5 \times 10^{10} M^{-1}$ for CEA, a value comparable to the parent T84.66 hybridoma. See Wagener, C., et al. *J. Immunol.* 130:2302–2307 (1983).

I claim:

1. A chimeric murine-human T84.66 antibody (ATCC Accession No. BH 8747) kappa gene having a murine variable region and a human constant region.

2. A chimeric murine-human T84.66 antibody (ATCC Accession No. BH 8747) gamma gene having a murine variable region and a human constant region.

* * * * *